US005866416A

United States Patent [19]

Mason et al.

[11] Patent Number: 5,866,416
[45] Date of Patent: Feb. 2, 1999

[54] CELL LINE FOR PROPAGATING RECEPTOR BINDING SITE-DELETED FMDV

[75] Inventors: Peter W. Mason, Killingworth, Conn.; Barry Baxt, Port Jefferson Station, N.Y.; Elizabeth Reider, Westbrook, Conn.; Analia Berinstein, Capital Federal, Argentina; Angray S. Kang, Carlsbad, Calif.

[73] Assignee: The United States of America as represented by the Secretary of Agriculture, Washington, D.C.

[21] Appl. No.: 593,999

[22] Filed: Jun. 24, 1996

Related U.S. Application Data

[63] Continuation-in-part of Ser. No. 418,716, Apr. 7, 1995, Pat. No. 5,612,040.

[51] Int. Cl.⁶ .......................... A61K 39/135; C07H 21/04; C07K 14/705; C12N 5/10
[52] U.S. Cl. ..................... 435/328; 435/7.21; 435/70.21; 435/236; 435/260; 435/325; 435/328; 435/339; 424/205.1; 424/216.1; 530/387.3; 530/388.3
[58] Field of Search ................. 435/7.21, 70.21, 435/236, 339, 325, 328, 260; 424/205.1, 216.1; 530/387.3, 388.3

[56] References Cited

U.S. PATENT DOCUMENTS 5,359,046 10/1994 Capon et al. .

OTHER PUBLICATIONS

Mason et al. "Antibody–Complexed Foot–and–Mouth Disease Virus, But Not Poliovirus, Can Infect . . . " Virology 192, pp. 568–577, 1993.
Crowther et al. Epidemiol. Inf., 1993, vol. 111, pp. 391–406.

*Primary Examiner*—Ponnathapura Achutamurthy
*Assistant Examiner*—Phuong T. Bui
*Attorney, Agent, or Firm*—M. Howard Silverstein; John D. Fado; Janelle S. Graeter

[57] ABSTRACT

A method of making a genetically-engineered cell line which is susceptible to infection by foot-and-mouth disease virus and allows the virus to replicate is disclosed. The method involves fusing the DNA encoding ICAM-1 with the DNA encoding an antibody specific for foot-and-mouth disease virus and expressing the resulting chimeric cell surface receptor protein. The chimeric cell surface receptor protein allows foot-and-mouth disease virus to bind, leading to subsequent infection and replication of foot-and-mouth disease virus. A genetically-engineered cell which expresses the chimeric cell surface receptor protein is also claimed.

5 Claims, 7 Drawing Sheets

```
                    Amino Acid Residue in VP1

130         140         150         160
             *           *           *           * pRMC35      Y NGTNKYSASG SGVRGDFGSL APRVARQLPA pRM-DRGD    - ---------- --D------- ----------
pRM-PRGD    - ---------- --P------- ----------
pRM-RGDK    - ---------- ------K--- -L-------- pRM-KGD     - ---------- ---K------ ----------
pRM-RGE     - ---------- -----E---- ----------
pRM-KGE     - ---------- ---K-E---- ----------
```

CELL LINE FOR PROPAGATING RECEPTOR BINDING SITE-DELETED FMDV

This application is a continuation-in-part of Ser. No. 8/418,716 filed Apr. 7, 1995 now U.S. Pat. No. 5,612,040.

BACKGROUND OF THE INVENTION

1. Field of the Invention

Foot-and-mouth disease virus (FMDV) is responsible for one of the most devastating and contagious diseases in cattle and other cloven-hooved animals, affecting over 100,000 animals a year and resulting in significant economic loss. The disease occurs in many areas of the world outside the United States where vaccination programs have been largely effective. There are risks associated with the vaccines currently in use, however, and at present FMDV vaccines cannot be produced in the United States despite the continued threat of the introduction of this agent into the country. It is feared that the virus used to make vaccines could escape from containment and cause disease. Moreover, the failure to completely inactivate the virus during vaccine preparation has led to accidental outbreaks of infection. In addition, there is considerable antigenic variability among the various serotypes, thus some viruses may not be recognized by the vaccinated animals. Furthermore, frequent revaccination has been required in order to maintain protective immunity utilizing conventional vaccines containing virus attenuated by chemical inactivation (Bachrach, H. L. 1968. Annu. Rev. Microbiol. vol. 22, pp. 201–244). There is thus a strong incentive to develop an effective vaccine which eliminates the threat of infection due to the accidental outbreaks associated with vaccine production and administration. A new and safer genetically-engineered vaccine against FMDV which provides effective protection but is not infectious, and thus does not present the risk of causing accidental infections, is the subject of related patent application Ser. No. 08/418,716 now U.S. Pat. No. 5,612,040. This invention relates to a genetically-engineered cell line for the propagation of the mutant virus.

2. Description of the Related Art

In an effort to overcome the deficiencies of conventional virus vaccines, synthetic vaccines have been investigated. Identification of a flexible loop exposed on the virus surface as the main antigenic site of FMDV (site A) prompted the investigation of the use of various peptide fragments within site A to stimulate immunological responses. For example, the conserved tripeptide Arg-Gly-Asp (RGD) was evaluated for its ability to stimulate the production of neutralizing antibodies in rabbits or guinea pigs (Novella et al. 1993. *FEBS Letters*. vol. 330, no. 3, pp. 253–259).

Attempts to produce attenuated virus vaccines by genetic engineering were also carried out. Rieder et al. (1993. *J. Virol*. vol. 67, no. 9, pp. 5139–5145, herein incorporated by reference), for example, evaluated the role of the poly(C) tract found at the 5' end of the FMDV genome. Cardioviruses having shorter-than-natural poly(C) tracts had been shown to be dramatically attenuated; however, the poly(C) tract length of FMDV showed no effect on virulence when tested in mice.

A non-infectious form of the FMD virus consisting of a genetically-engineered receptor-binding site-deleted virus particle has been described in related U.S. Pat. No. 5,612,040, supra. The receptor binding site-deleted particle, which lacks the three amino acids of the tripeptide RGD in the capsid protein VP1 is not infectious for cells in culture or for animals; however, the RGD-deleted virion is able to induce a protective immune response in cattle U.S. Pat. No. 5,612,040, supra; McKenna et al. 1995. *J. Virol*. vol. 69, p. 5787). Since the virus cannot infect cells in culture or animals, production of the virus has been limited to the transfection of cells capable of allowing assembly of the mutant virus from the vector containing the mutant RNA, allowing RNA to replicate in the transfected cells and harvesting the mutant virus particles from the cell cultures. Although effective, it is expensive to produce commercial quantities of virus in this manner. Thus a means for the production of virus in larger quantities was needed.

SUMMARY OF THE INVENTION

To overcome this problem, we have now engineered a cell line capable of growing the virus which has a novel cellular receptor molecule derived from a recombinant DNA produced by fusing the gene for the active site of an antibody specific for the virus to the gene for a normal cell surface protein. The chimeric protein thus produced confers viral susceptibility to cells that normally lack the receptor, thereby producing a cell line useful for the mass cultivation of the receptor-deleted mutant virus. In accordance with this discovery, it is an object of the invention to provide a novel genetically-engineered cell line susceptible to infection by receptor-deleted FMD virus particles and capable of allowing replication of the virus to occur.

It is another object of the invention to provide a method of making the novel genetically-engineered cell line.

Other objects and advantages of the invention will become readily apparent from the following description.

DETAILED DESCRIPTION OF THE INVENTION

A vaccine is defined herein as a biological agent which is capable of stimulating a protective immune response in an animal to which the vaccine is administered.

Foot-and-mouth disease virus is an RNA virus of the Aphthovirus genus of the family Picornaviridae. There are several known serotypes occurring in Europe (A, O and C

TABLE 3

Growth of wild-type FMDV in wild-type and transfected CHO cell cultures.

| CHO cell culture[1] | Virus yield (pfu/ml)[2] |
|---|---|
| pscAb/ICAM-1#11-transfected | $9.5 \times 10^5$ |
| $pV_HK\#2$-transfected | $2.0 \times 10^3$ |
| wild-type cells | $1.6 \times 10^3$ |

[1]Cells were second-passage, G418- selected cells or wild-type cells.
[2]Cells were grown in 35 mm diameter dishes, inflected at a multiplicity of infection (moi) of 20 for one hour at 37° C., rinsed in MES-buffered saline, pH 6.0 to remove input virus, incubated overnight at 37° C., lysed by freeze/thaw, and virus titers determined by plaque assay (Rieder et al., 1993. J. Virol. 67, 5139).

serotypes), southern Africa (SAT 1, SAT 2 and SAT 3) and the Asia 1 serotype, having distinct variations both immunologically and genetically. The virion consists of a single-strand, positive-sense RNA genome packaged in an icosahedrally symmetric shell composed of 60 copies each of four structural proteins, VP1-4. Analysis of the three-dimensional structure of FMDV revealed a prominent surface feature formed by a flexible loop between the G and H β strands of VP1 (G-H loop) (Acharya et al. 1989. *Nature*. vol., 337, p. 709; Parry et al. 1990. *Nature*. vol. 347, p. 569; Logan et al. 1993. *Nature*. vol. 362, p. 566). Contained within this loop is the highly conserved RGD tripeptide sequence which has been identified as the main antigenic site. In addition, synthetic peptide inhibition studies have suggested that the site is also involved in receptor binding activity (Fox et al. 1989. *J. Gen. Virol.* vol. 70, p. 625; Baxt and Becker. 1990. *Virus Genes*. vol. 4, p. 73).

Studies were carried out in order to further elucidate requirements for cell binding, immunogenicity and the infectious ability of the virus. For this purpose, mutant viruses were prepared from a full-length infectious cDNA clone of FMDV type $A_{12}$ (Rieder et al., supra), where amino acid substitutions were made either within or bordering the conserved RGD sequence (as described in Mason et al. 1994. *PNAS*. vol. 91, pp. 1932–1936, herein incorporated by reference).

Figure 1:
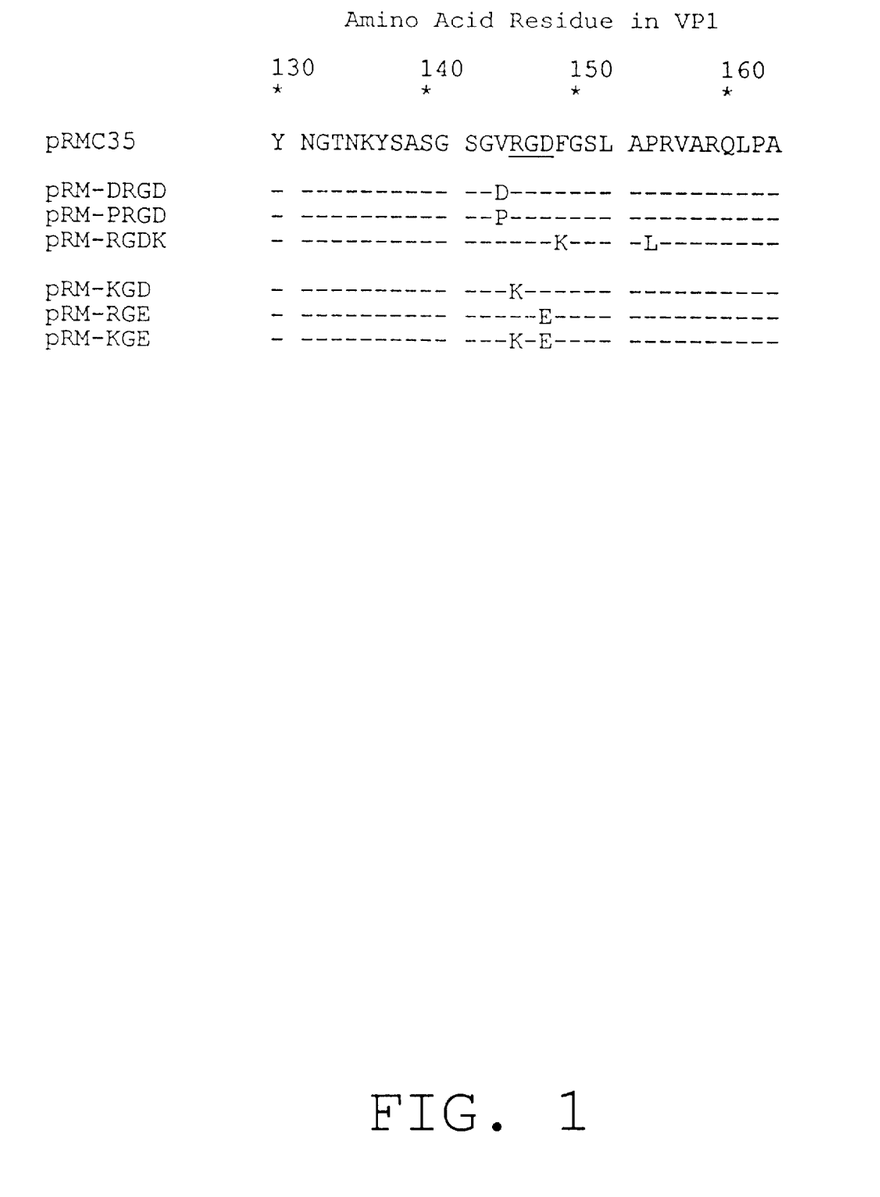
FIG. 1 shows the amino acid sequences of the G-H loop of the wild-type and mutant genomes. Dashes designate identity with wild-type.

Full-length mutant cDNA molecules having sequence changes as shown in FIG. 1 in codons 143–147 of VP1 were produced. Antigenic properties of mutant viruses produced from the cDNAs were evaluated by reacting the viruses with a panel of monoclonal antibodies which recognized epitopes either within or outside the G-H loop. Results, shown in Table 1, indicated that conservative changes within the G-H loop did not induce major changes in the antigenic structure of the virion.

TABLE 1

| Sequence * | Antibody Reactivity** | Cell Binding, % + |
|---|---|---|
| VRGDF (Wild-type) | + | 65 |
| DRGDF | + | 28 |
| PRGDF | + | 61 |
| VRGDK‡ | ± | 63 |
| VKGDF | + | 2 |
| VRGEF | + | 2 |
| VKGEF | + | 2 |

*Amino acids 143–147 of VP1 (underline denotes mutations)
**Determined by radioimmunoprecipitation: +, strong reaction, ±, weak reaction
+ Determined at a constant virus/cell ratio (1000:1)
‡Also contains a leucine substitution for a proline at position 152 (see FIG. 1)

Cell binding studies utilizing the mutant viruses were also carried out. Binding of the viruses having mutations bordering the RGD sequence to baby hamster kidney (BHK) cells were retained; however, cell binding was somewhat reduced in two of the three mutants and reduced by about 50% in the third. Those mutants having mutations within the RGD sequence did not bind to BHK cells, however, indicating that they were defective with respect to binding and adsorption into the cell (Table 1).

Transcripts of the various mutant sequences were evaluated for their ability to cause cytopathic effects (CPE) and produce plaques following transfection into BHK cells. Those transcripts having mutations bordering the RGD sequence caused CPE, plaques and specific infectivities similar to transcripts from the parental infectious clone (Table 2), indicating that mutations encoded by these RNAs had no effect on viability.

The mutant viruses were found to be antigenic but not infectious, however single base mutations have been known to revert to wild-type. Tests were thus carried out to determine if reversions occurred as expected for the mutant viruses. Cells transfected with mutant RNA containing KGD and RGE mutations were found to produce 10,000-fold less infectious virus than cells transfected with RNA produced from the wild-type virus. Sequence analysis of selected plaques harvested from transfected cells confirmed that those viruses found to be infectious had regained the RGD coding sequence. As also expected, the double mutation KGE did not appear to revert to wild-type since no plaque-forming units were recovered from cells transfected with the double-mutant RNA. In addition, all of the KGD and RGE revertants produced wild-type plaques, and a detailed examination of cell binding by one of these revertants revealed that it bound to cells as well as the wild-type virus, conclusively showing that the RGD sequence is required for adsorption to and infection of BHK cells.

TABLE 2

| Sequence* | Specific Infectivity** |
|---|---|
| VRGDF (Wild-type) | $4.2 \times 10^3$ |
| DRGDF | $6.6 \times 10^3$ |
| PRGDF | $2.0 \times 10^3$ |
| VRGDK | $1.4 \times 10^3$ |
| VKGDF | <1 |
| VRGEK | <1 |
| VKGEF | <1 |

*Amino acids 143–147 of VP1 (underline denotes mutation)
**Specific Infectivity of transcripts (plaque-forming units/µg) determined using Lipofectin Since the threat of reversion to wild-type is clearly not a desirable property for a virus contemplated for use as a vaccine, especially one having virulence such as that exhibited by FMDV, efforts to create a stable non-infectious FMDV were begun. A virus was constructed in which the entire RGD sequence was deleted, and tests were carried out to determine the effect of the deletion on the conformation of the capsid structure, and thus the antigenicity of the virus. A genome-length cDNA (Rieder et al., supra) was prepared from the wild-type RNA, and the codons encoding the wild-type amino acid sequence GVRGDF were replaced with codons for AsnPro (NP). Synthetic RNA transcripts were constructed from this cDNA and introduced into BHK cells (Mason et al., supra). Cells transfected with the synthetic RNA produced levels of virus particles similar to those produced by cells transfected with wild-type RNA, and preliminary experiments showed that these particles did not bind to cells, were non-infectious, and were recognized by monoclonal antibodies specific for four different epitopes on FMDV type $A_{12}$ (Baxt et al. 1984. *J. Virol.* vol. 51, p. 298; Baxt et al. 1989. *J. Virol.* vol. 63, p. 2143). One of these epitopes included portions of the G-H loop, indicating that the deletion had little, if any, effect on the antigenic structure of the RGD-deleted virus.

Tests were also carried out to demonstrate that the RGD-deleted mutant viruses would not revert to wild-type with respect to infectivity or virulence (see Example 2). RGD-deleted mutant virus preparations were used to inoculate BHK cells and baby mice. No CPE were observed in BHK cell cultures which had been incubated for 72 h, and a plaque assay carried out on passaged cells did not reveal any infectious agent. In addition, 20 7- to 10-day-old mice were inoculated, and none of the mice died or showed any signs of infection.

Virulence of the mutant virus was tested by inoculating swine with either mutant or wild-type virus (see Example 3). Virus was inoculated into the coronary band and the dermis of the snout of two adult Yorkshire swine, and the animals were observed for signs of FMD for 2 weeks. Symptoms of classical FMD were observed in the animal having received the wild-type inoculation, whereas the animal receiving mutant virus inoculations showed no signs of disease.

Tests were also carried out to demonstrate the efficacy of the vaccine (see Example 4). A vaccination/challenge study with nine 18- to 20-month-old steers was conducted. Three steers were mock vaccinated, three animals were vaccinated with a conventional inactivated wild-type virus and the remaining three animals were vaccinated with the mutant RGD-deleted virus. The animals were observed for signs of disease for 4 weeks, and none showed any development of disease.

To further test the effectiveness of the mutant virus, the nine animals were subsequently combined in a single room and exposed to a pig which had developed severe clinical manifestations of FMD. The cattle were examined daily for signs of the disease. All six vaccinated animals were protected whereas all three mock-vaccinated animals demonstrated clinical FMD within 7 days of exposure to the infected pig.

Preparation of the mutant virus is carried out by conventional genetic engineering techniques which are well-established in the art (as described, for example, in *Current Protocols in Molecular Biology*. 1994. Ausubel et al., eds. J. Wiley & Sons, NY). The preparation steps include 1) synthesizing cDNA from infectious RNA, 2) replacing the sequences coding for GVRGDF with NP, 3) transcribing RNA containing the deleted sequences from the mutant CDNA, 4) cloning the mutant synthetic RNA into an effective vector, 5) transfecting cells capable of allowing assembly of the mutant virus from the vector containing the mutant RNA, 6) allowing the RNA to replicate in the transfected cells in order to produce mutant virus particles and 7) harvesting the mutant virus particles from the cell cultures. A complete description of the method of preparing the mutant virus is contained in parent application now U.S. Pat. No. 5,612,040, supra, herein incorporated by reference.

Synthetic mutant RNAs are transcribed and introduced into cells capable of allowing replication of the mutant viruses. BHK cells have been found effective for this purpose; however, other cell lines such as Chinese hamster ovary (CHO) are also useful. The cells may be effectively transfected using Lipofectin (GIBCO/BRL) or electroporation as described in Mason et al., supra. Using the electroporation method described in Example 1, large numbers of cells transfected with the RGD-deleted RNA are produced, cultured and mutant virus particles are found in the culture medium. Any effective culture medium may be used, for example Eagle's minimum essential medium with 10% calf serum and 10% tryptose phosphate broth, supplemented with antibiotics. The mutant virus may then be harvested from the cultures and purified for use as a vaccine. While this method is effective for producing the novel virus, utilization of the genetically-engineered cell line described herein is advantageous in that the production of larger quantities of virus is facilitated.

The first step of infection of cells in culture or in animals by FMDV is the attachment of the virus to specific cell surface molecules. An RGD-specific cell surface integrin, alphav/beta3, is the receptor for type $A_{12}$ FMDV on cultured cells (Berinstein et al. 1995. *J. Virol.* vol. 69, p. 2664), consistent with the finding that the RGD-deleted virus cannot bind to or infect cells (McKenna et al., supra).

Since initiating the infectious cycle requires the binding of the virion to the surface of susceptible cells (Mason et al. 1993. *Virol.* vol. 192, p. 568), a cell surface receptor composed of a well-characterized cell surface molecule and the virus binding end of an antibody specific for FMDV was engineered, using standard molecular biology methods (as described, for example, in Ausubel et al., supra).

The cell line is prepared essentially by carrying out the following steps:

1) selecting an effective cell line;
2) selecting a cell surface protein and obtaining the DNA which encodes that protein;
3) selecting an antibody specific for FMDV and obtaining the DNA which encodes that antibody;
4) fusing the two DNAs for form a chimeric DNA;
5) inserting the chimeric DNA into a eucaryotic expression vector;
6) transfecting the selected cell line; and
7) testing the tranfected cells to determine if chimeric DNA has been incorporated.

In selecting an effective cell line, while not required, a cell line which is not susceptible to infection by FMDV is advantageous in that selection and testing of transformed cells is facilitated.

Figure 3:
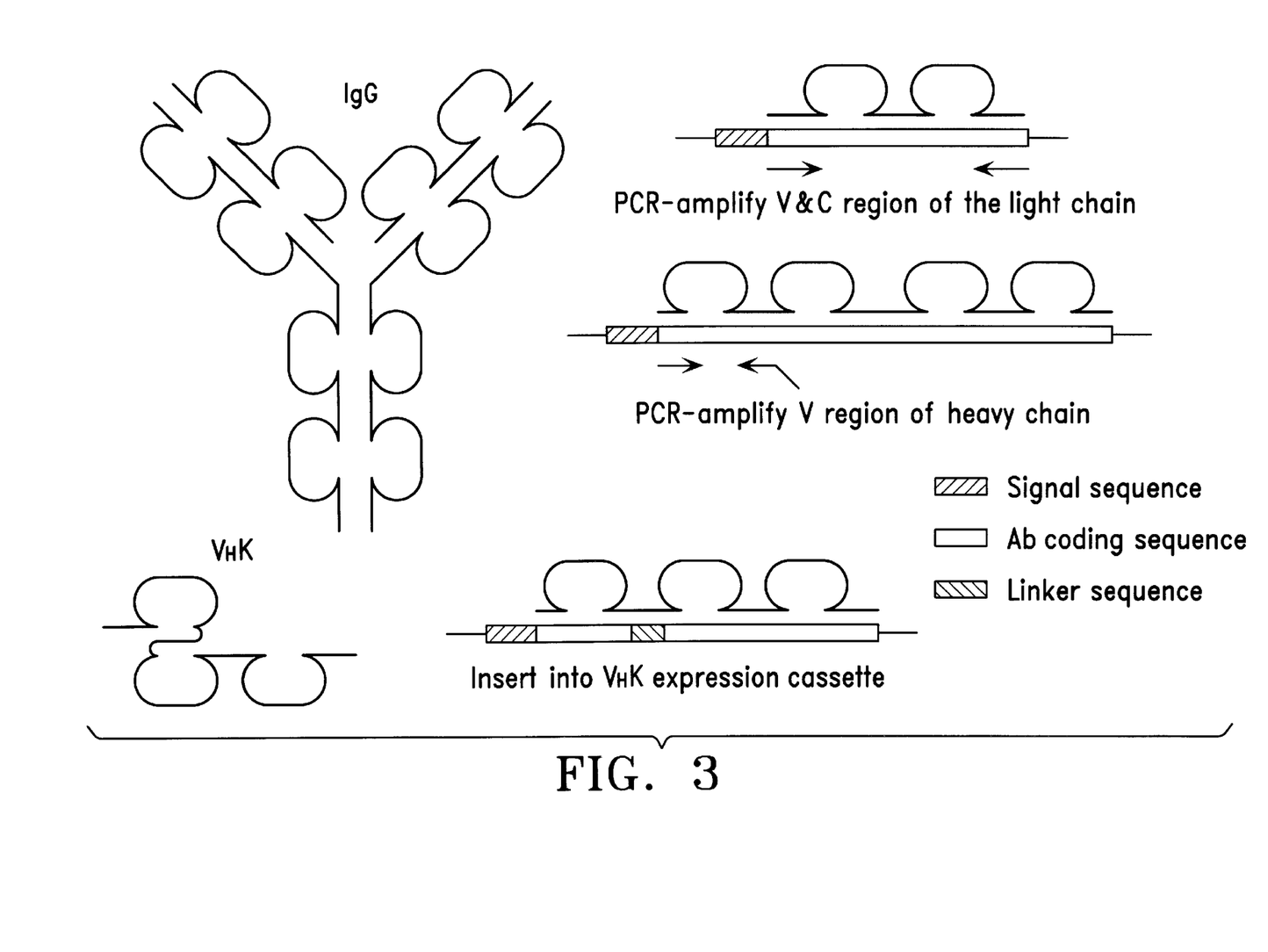
FIG. 3 shows a method for single chain antibody production.

Specifically, the cDNAs for the variable (virus-binding) domains of the messenger RNAs (mRNAs) encoding the heavy and light chains of an FMDV-specific monoclonal antibody (MAb) were amplified (FIG. 3). While any monoclonal antibody specific for FMDV is considered useful for this purpose, the MAb 2PD11 described by Baxt et al. was utilized (Baxt et al., 1984, supra; Baxt et al., 1989, supra). Initially, the variable V region of the heavy chain and the V and constant C regions of the light chain were amplified, then assembled into the gene for a single-chain antibody molecule (scaB) in a bacterial plasmid [(FIG. 3); He et al. 1995. *Immunol.* vol. 84, p. 662). Bacteria carrying this plasmid were induced to produce the gene product, and preparations of the induced bacterial cultures were tested for their ability to immunoprecipitate radiolabeled virus particles. In these tests, the scAb was shown to be active.

Figure 4:
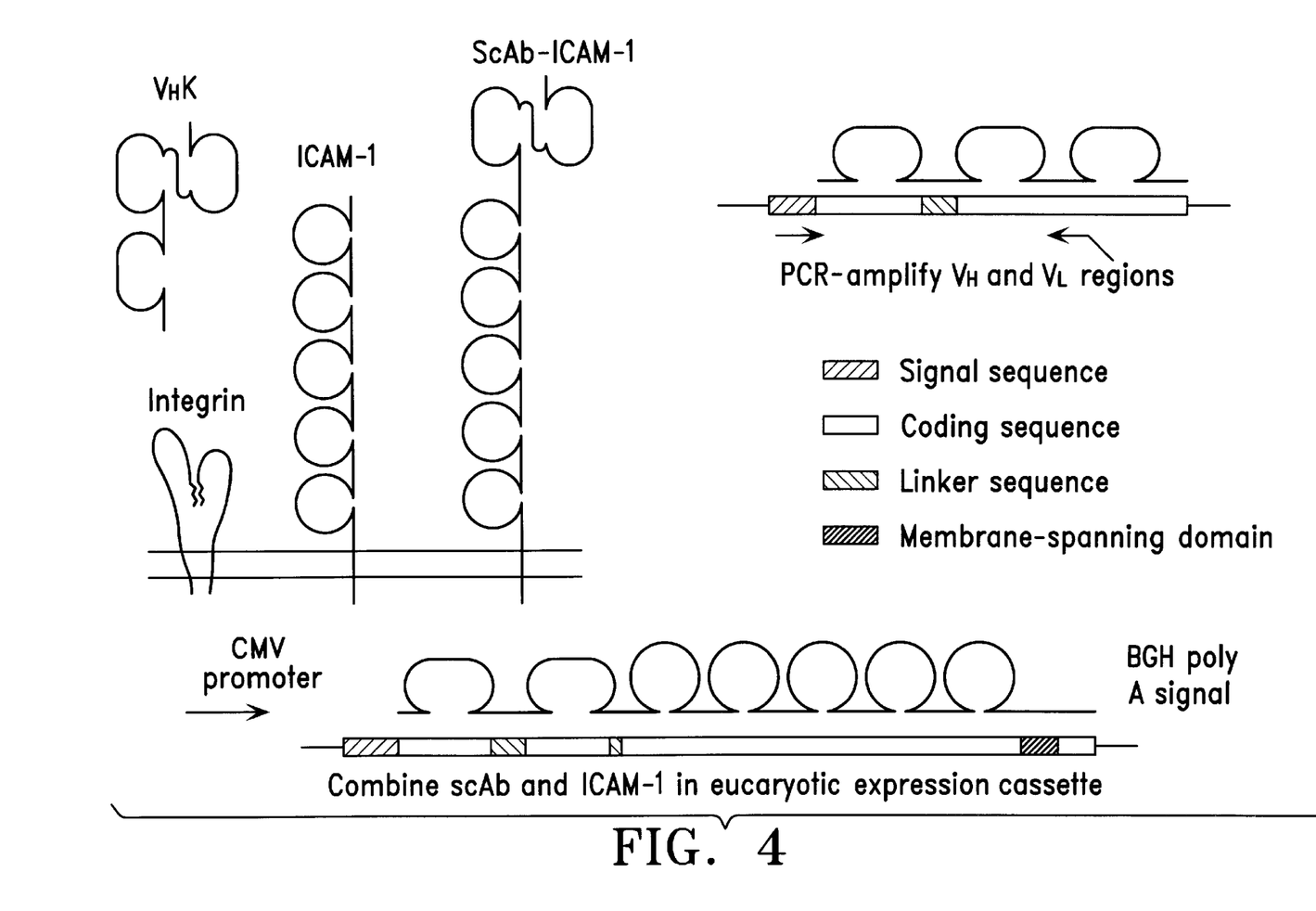
FIG. 4 shows production of scAb-1CAM-1 receptor.

The next step was fusion of the scAb CDNA to the CDNA for intracellular adhesion molecule 1 (ICAM-1), a well-characterized cell surface molecule known to serve as the receptor for another group of picornaviruses, the rhinoviruses (Staunton et al. 1989. *Cell.* vol. 56, p. 849; Tomassini et al. 1989. *PNAS.* vol. 86,j p. 4907). Using standard techniques (Ausubel et al., supra), the two cDNAs were fused and inserted into the eucaryotic expression plasmid, pcDNA3 (Invitrogen, San Diego, Calif.) behind a cytomegalovirus (CMV) promoter and an IgG signal sequence, and in front of a bovine growth hormone polyadenylation signal (FIG. 4). While the above conditions have proven effective, the selection of alternative cell surface proteins, expression plasmids, promoters, etc. are well within the level of skill in the art.

The plasmid harboring the scAb-ICAM-1 fusion (designated pscAb-ICAM-1#11) was transfected into Chinese hamster ovary (CHO) cells (Mason et al., 1993, supra), using Lipofectin (Life Technologies, Inc., Gaithersburg, Md.). Transformed cells were selected in the presence of 0.6 mg/ml of the eucaryotic antibiotic, G418 (Life Technologies, Inc.) using standard CHO cell propagation methods (Mason et al., 1993, supra). Following two passages in G418, cultures prepared from cells transfected with pscAb/ICAM-1#11 were able to replicate FMDV, whereas wild-type CHO cells, or cells transfected with the plasmid encoding only the scAb (designated $Pv_HK\#2$) were not susceptible to infection (Table 4). Although these results provided the first evidence that the scAb/ICAM-1#11 molecule could serve as an FMDV receptor, the titers of virus recovered from the pscAb/ICAM-1#11-transfected cultures were much lower than those obtained in previous studies of CHO cells expressing the Fc receptor and infected with antibody-complexed virus (Mason et al., 1993, supra).

The lower-than-expected titer of virus harvested from these cultures was consistent with the fact that the type $A_{12}$ virus did not kill all of the cells in these cultures, suggesting that not all of the cells in the culture were expressing functional scAb-ICAM-1 receptors. Therefore, single-cell clones were prepared from these transfected cultures and tested for their ability to be killed by virus. These experiments identified several clones that showed nearly uniform virus-induced cell death, or cytopathic effect (CPE), when infected with virus. One transfected CHO cell clone, designated SHO 11.1 was expanded and further tested.

Figure 5:
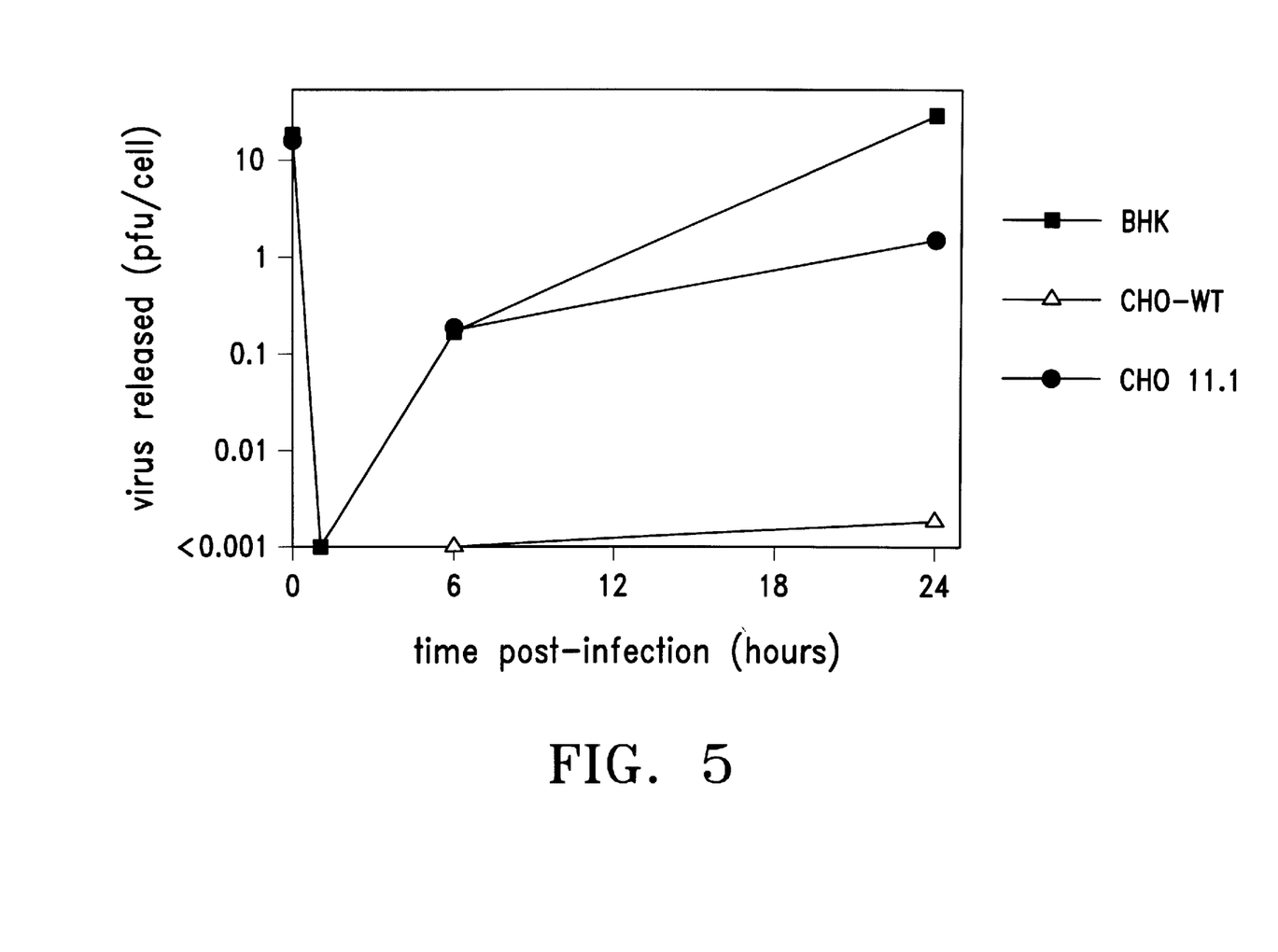
FIG. 5 shows one-step growth curves of wild-type FMDV type A12 released from infected BHK, CHO-WT, and CHO 11.1 cells. Arrow indicates the time of low pH rinse, see Table 3.

One-step growth curves with type $A_{12}$ confirmed that the CHO 11.1 cell line produced high titers of virus, whereas wild-type CHO cells did not (FIG. 5). The amount of virus recovered from this cell line was similar to that recovered from infected BHK cells (FIG. 5). Furthermore, wild-type virus was able to form plaques on the CHO 11.1 cell line, whereas a previously

TABLE 4

Plaque-forming ability of wild-type type A12 FMDV and B2PD.3 on CHO11.1 and BHK cells.

| virus | titer in pfu/ml[a] | |
|---|---|---|
| | CHO 11.1 | BHK |
| wild-type FMDV | $2.7 \times 10^7$ | $4.5 \times 10^8$ |
| B2PD.3[b] | $5 \times 10^{2c}$ | $1.0 \times 10^8$ |

[a]Titers determined by staining monolayers at 2 days post infection.
[b]2PD11 MAb escape mutant (see Baxt et al., 1989).
[c]Diffuse plaques.

TABLE 5

| Animal | Vaccine | Neut titer ($\log_{10}$ $PRN_{70}$) | Response to challenge | |
|---|---|---|---|---|
| | | | Fever | Lesions |
| 57 | | <0.7 | + | + |
| 109 | No vaccine | <0.7 | + | + |
| 148 | | <0.7 | + | + |
| 15 | | 3.4 | − | − |

TABLE 5-continued

| Animal | Vaccine | Neut titer ($\log_{10}$ $PRN_{70}$) | Response to challenge | |
|---|---|---|---|---|
| | | | Fever | Lesions |
| 103 | RGD-deleted | 2.5 | − | − |
| 143 | | 2.5 | − | − |
| 21 | | 2.5 | − | − |
| 50 | BEI-inactivated | 2.8 | − | − |
| 101 | | 2.2 | − | − | characterized 2PD11 monoclonal antibody escape variant B2PD.3 (Baxt et al., 1989, supra) could not (Table 4).

Figure 6:
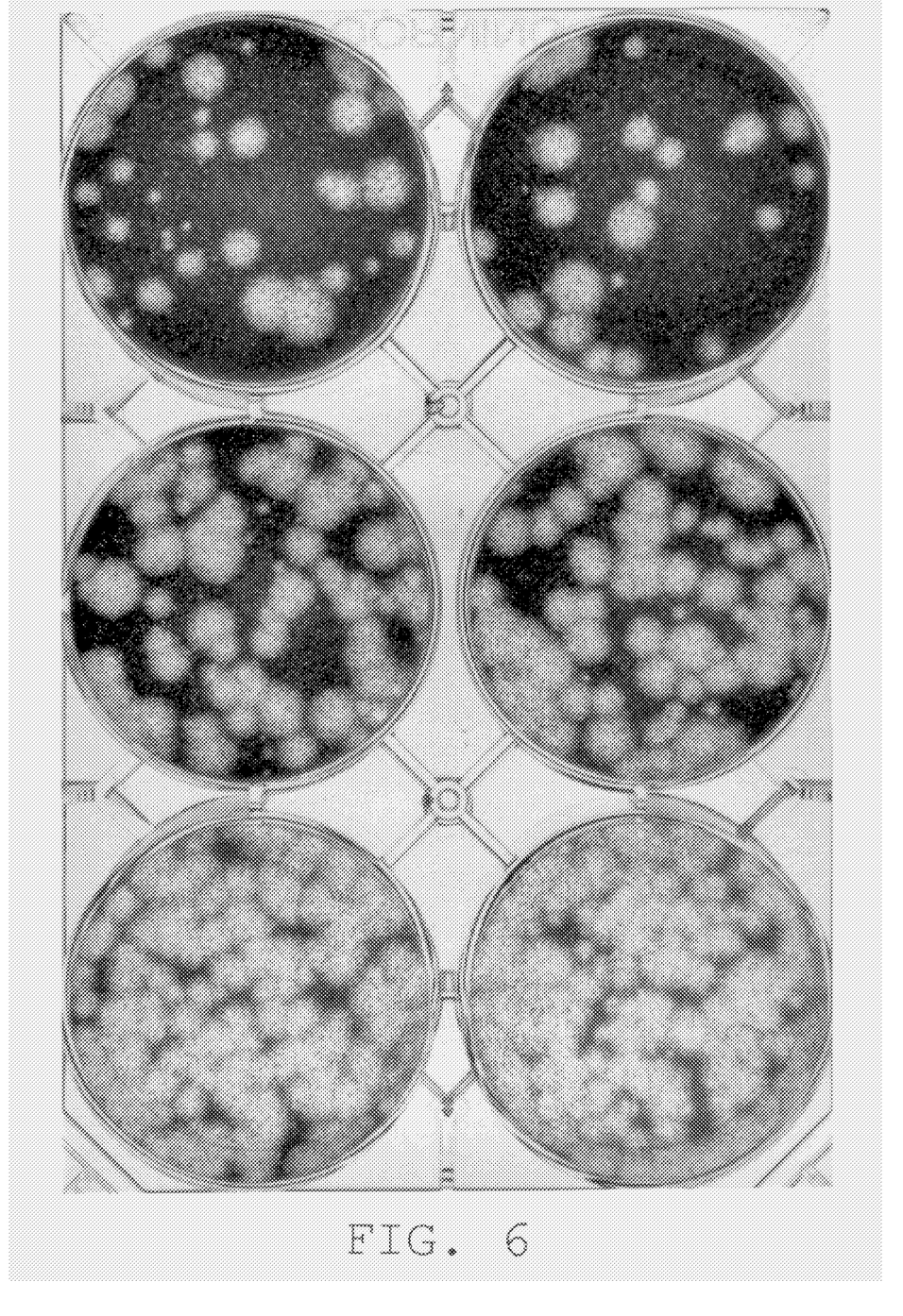
FIG. 6 shows plaques formed by the RGD-FMDV on monolayers of CHO 11.1 cells. Cells were infected with dilutions of virus, overlayed with tragacanth, and stained 72 hrs post infection by standard methods.
Figure 7:
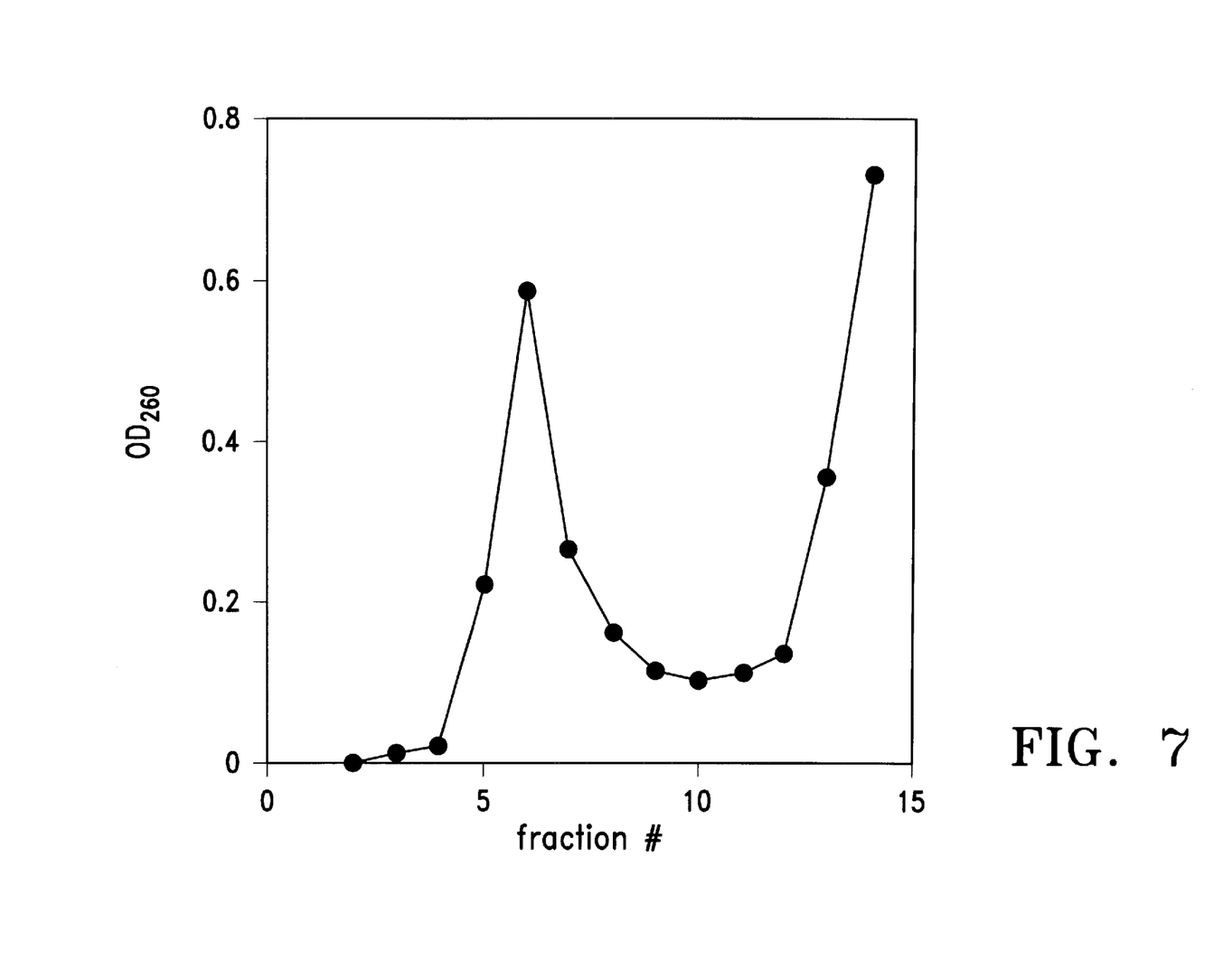
FIG. 7 shows A260 profile of sucrose density gradients prepared from RGD-virus grown in CHO 11.1 cells.

Since the portion of the virus that binds to the natural cellular receptor is distinct from the site recognized by 2PD11, which is in the G-H loop of the capsid protein VP3 (Baxt et al., 1989, supra), tests were carried out to determine if the RGD-deleted deleted type $A_{12}$ virus (McKenna et al., supra; U.S. Pat. No. 5,612,040, supra) was able to infect the CHO 11.1 cells. FIG. 6 shows that the RGD-deleted virus was able to form plaques on these cells, consistent with the findings that the virus caused uniform CPE in this cell line. Furthermore, standard methods of virus cultivation yielded high levels of the RGD-deleted virus (FIG. 7). Data shown in FIG. 7 correspond to a production of over 1.5 μg purified RGD- virus from $10^6$ CHO 11.1 cells, a value comparable with the 1.1 μg yield of purified wild-type $A^{12}$ virus from 106 BHK cells. Moreover, when $1 \times 10^7$ plaque forming units (pfu) of the CHO 11.1-propagated RGD-deleted virus was inoculated into the tongue of a bovine (as described by Cottral et al., 1965. Bull off. Int. Epiz. vol. 63, p. 1607), no lesions were formed, and the animal did not display fever or lameness, indicating that the RGD-deleted virus propagated by this method was over $10^6$-times less infectious in bovines than type $A_{12}$ virus (Cottrall et al., supra).

It has thus been shown that the scAb-ICAM-1-expressing cells are capable of producing large amounts of the RGD-deleted virus particles obtained from cells transfected with the RGD-deleted full-length RNA (U.S. Pat. No. 5,612,040, supra; McKenna et al., supra). The scAb-ICAM-1 plasmid is specific for the type $A_{12}$ virus, therefore antibodies used to manufacture receptors for other serotypes and subtypes of FMDV may need to be specific for those particular types. Furthermore, the selection of ICAM-1 as the cell surface protein is not considered an essential requirement for the production of a viable genetically-engineered receptor, i.e. any effective cell surface protein would be useful. Moreover, any effective eucaryotic expression plasmid is useful for transfection and expression of the receptor. Alternative methods (e.g., stable transformation by DNA integration) can also be used to generate cell lines expressing chimeric antibody-based receptors that will function for the replication of the receptor binding site-deleted virions. In addition, the cells may be cultured by conventional incubation techniques which are known in the art for the particular wild-type cell utilized. Mutant virus is harvested by collecting the culture media and separating the virus from the media.

Vaccines are prepared for inoculation by mixing an effective immunization dosage of the mutant virus in a pharmaceutically acceptable carrier or diluent, such as physiological saline or tissue culture medium. An effective immunization dosage is defined as that amount which will induce immunity in an animal against challenge by a virulent strain of FMDV, and immunity has been considered having been achieved when the level of protection for the immunized population is significantly higher than that of an unvaccinated control group. An effective dosage is easily determined by one of skill in the art for the particular animal of interest by administering varying amounts of the vaccine preparation to test animals and observing the dosage at which protection has been achieved.

In addition, appropriate adjuvants as known in the art may also be included in the vaccine formulation.

The following examples are intended only to further illustrate the invention and are not intended to limit the scope of the invention as defined by the claims.

EXAMPLES

Example 1

Preparation of Synthetic Mutant FMDV

Figure 2:
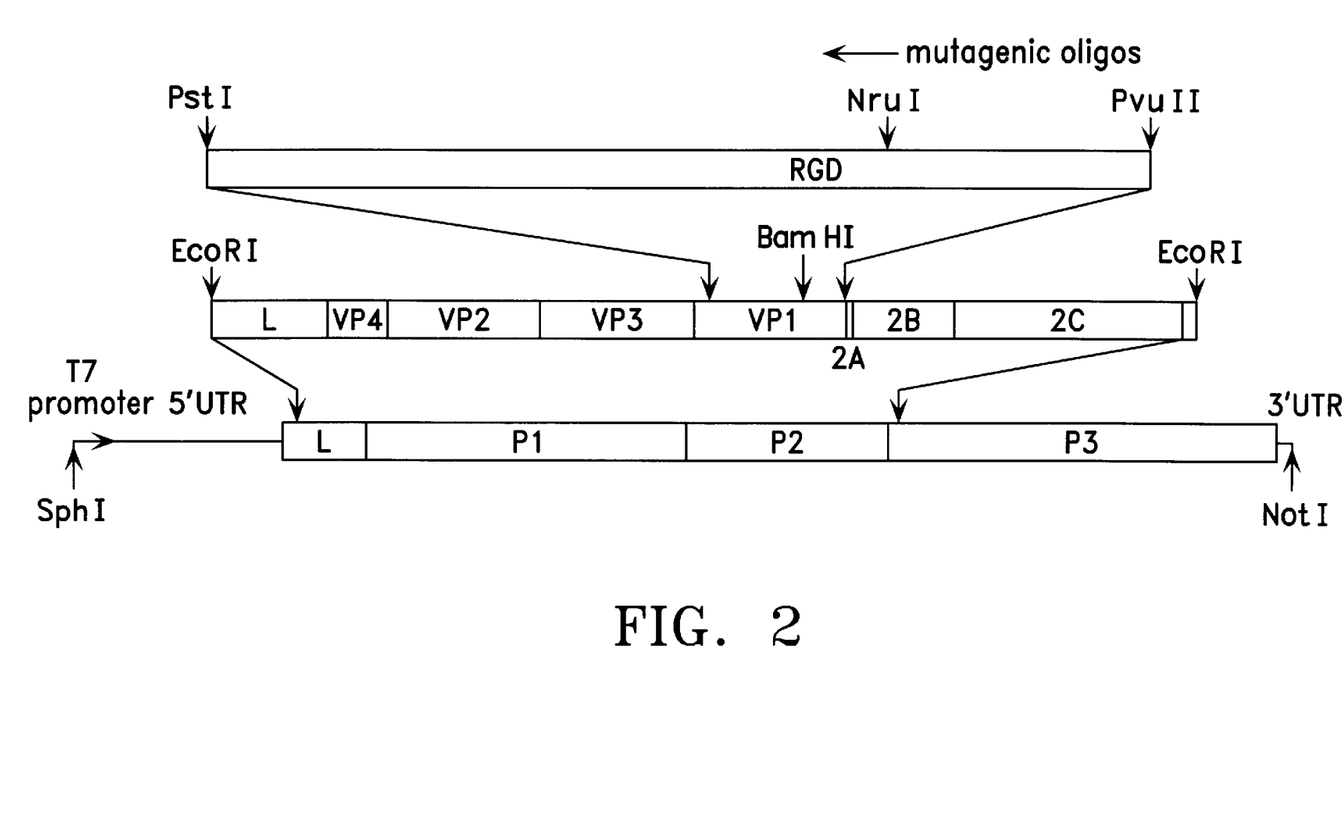
FIG. 2 shows the position of mutated sequences on the FMDV genome. CDNA fragments used to engineer mutant viruses are shown above the FMDV portion of the plasmid pRMC$_{35}$. UTR, untranslated region; oligos, oligonucleotides.

FMDV RNA is isolated and purified from FMDV and used to produce cDNA by reverse transcription using AMV reverse transcriptase (Boehringer Mannheim) or Moloney murine leukemia virus (MMLV) reverse transcriptase (GIBCO/BRL). Mutations in the cDNA molecule are carried out according to the method presented in FIG. 2. Double-stranded DNA is then produced by filling in with DNA-dependent DNA polymerase and is cloned into the PGEM plasmid. Plasmids containing virus cDNAs are identified and assembled into genome-length cDNA molecules and placed under the control of the T7 bacteriophage polymerase promoter. Plasmid DNA molecules containing the full-length cDNA are purified from cultures of $E.\ coli$ which harbor the plasmids, then used as a template for T7 RNA polymerase to produce synthetic genome-length RNAs containing the RGD deletion in the viral genome.

Electroporation is carried out by mixing 0.8 ml BHK cells at $3 \times 10^7$ cells per ml of $Ca^{2+}$- and $Mg^{2+}$-free phosphate buffered saline with 10 to 20 $\mu$g of RNA in a 0.4-cm cuvette, pulsed twice at 1500 V and 14 $\mu$F in an IBI Gene Zapper (IBI, New Haven, Conn.), diluted with growth medium (Eagle's MEM, 10% calf serum) and incubated in culture plates for 2–4 hours prior to removal of unattached cells and incubation overnight at 37° C.

The virus particles present in the culture fluid are harvested from the BHK cell cultures, concentrated by polyethylene glycol precipitation and further purified by sucrose density gradient centrifugation (Baxt et al., 1984 and 1989, supra).

The amount of virus present in these partially purified preparations was estimated by comparison of the radioactive signals obtained on Western blots (Towbin et al. 1979. *PNAS*. vol. 76, p. 4350) with two-fold dilutions of a known concentration of wild-type virus, detected using polyclonal guinea pig serum specific for FMDV and $^{125}$I-labeled protein A (NEN, Boston, Mass.). Approximately 1 $\mu$g of partially purified RGD-deleted virions could be obtained from $6 \times 10^6$ transfected cells.

Example 2

Inoculation into BHK Cells and Mice

BHK cells and baby mice were inoculated with the RGD-deleted virus preparations in order to demonstrate that the RGD-deleted virus would not regain its infectivity or virulence. Five hundred ng of RGD-deleted virus were diluted in culture media, inoculated into cultures of BHK cells, and incubated for 72 h at 37° C. Although no cytopathic effect (CPE) was visible at this time, the sample was lysed by freeze-thaw, and passaged onto fresh cells. A plaque assay of this second passage material on BHK cells did not reveal any infectious agent. One hundred ng of RGD-deleted virus were inoculated intraperitoneally (IP) into 20 seven- to ten-day-old mice. None of these mice died or showed any signs of infection. One hundred ng of a wild-type virus prepared from cells transfected with RNA derived from the wild-type genome-length cDNA, pRMC$_{35}$ (Rieder et al., supra), is equivalent to $1.2 \times 10^6$ mouse LD$_{50}$. These results demonstrate that the RGD-deleted virus is attenuated greater than $1 \times 10^6$ fold relative to wild type.

Example 3

Inoculation of Swine

Two $\mu$g of either wild-type or RGD-deleted virus were inoculated into the coronary band and the dermis of the snout of two adult Yorkshire swine. The animals were observed for signs of FMD for 2 weeks. The animal receiving 2 $\mu$g of wild-type virus developed classical FMD (fever and lameness with vesicles on all four feet and the snout) within 5 days of inoculation, whereas the animal inoculated with 2 $\mu$g of the RGD-deleted virus did not show any signs of disease. As expected, radioimmunoprecipitation analyses of serum collected 28 days postinfection from the animal inoculated with the wild-type virus revealed strong reactivity to structural proteins as well as the non-structural proteins 3D and 2C, indicating that the virus had replicated in the animal (Berger et al. 1990. *Vaccine*. vol. 8, p. 213). In contrast, the 28-day postinoculation sera obtained from the pig inoculated by this route with the RGD-deleted virus showed very low levels of reactivity with structural proteins, and no detectable reactivity with non-structural proteins, indicating that the RGD-deleted virus did not replicate in this animal (Berger et al., supra).

Example 4

Inoculation of Cattle

To test the usefulness of the RGD-deleted virus as a vaccine, a vaccination/challenge study with nine 18- to 20-month-old Hereford steers was conducted. Three steers were mock vaccinated with a tissue culture media/mineral oil emulsion, three animals were vaccinated with sucrose gradient-purified, binary ethylenimine (BEI)-inactivated (H.G. Bahnemann. 1975. *Arch. Virol*. vol. 47, p. 47) wild-type virus emulsified in oil, and the remaining three animals were vaccinated with an oil emulsion containing RGD-deleted virus. Animals were observed for signs of FMD for 4 weeks, and in that time none of the animals developed fever or vesicles of FMD. Four weeks postvaccination, serum was collected from all nine animals, and tested for its ability to neutralize the virus in vitro. These assays showed that the RGD-deleted virus was indistinguishable from the BEI-inactivated preparation in its ability to elicit neutralizing antibodies in cattle (Table 5).

The nine animals listed in Table 5 were combined in a single large room and exposed to a pig which had developed severe clinical manifestations of FMD after infection with a virulent cattle-passaged strain of FMDV type A$_{12}$ (Vallee strain 119, cattle passage 78; kindly provided by Dr. J. House). The cattle were examined daily for onset of clinical signs (lameness, vesicle formation on the tongue, or fever). If temperatures over 39° C. were noted, the animals were sedated and examined closely for vesicular lesions on their feet and in their mouths. All six vaccinated animals were protected from clinical disease, whereas all three mock-vaccinated animals demonstrated clinical FMD with fevers (3 days over 40° C.) and lesions on the tongue and all four feet within 7 days of exposure to the infected pig.

Effectiveness of the vaccine was further evaluated by determining if viral challenge had produced immune responses to viral antigens, i.e. by comparing the ability of pre- and postchallenge sera to precipitate viral proteins from radiolabeled infected cell lysates. For one animal (#143), a weak reaction to protein 3D was observed in prechallenge sera, consistent with the fact that antibodies to 3D are often observed in sera from vaccinated animals (Berger et al., supra). Antibodies to non-structural proteins 2C, 3AB and 3C were present in postchallenge sera of mock-vaccinated animals. Based on previously established criteria (Berger et al., supra), the presence of antibodies to two or more of these antigens demonstrates extensive viral replication, consistent with the observed clinical signs in these animals (Table 6). Several minor differences between pre- and postchallenge sera were also noted among the six vaccinated animals, and in several cases antibodies to 3D were detected in postchallenge sera. However, following challenge none of the vaccinated animals developed antibodies to 2C, 3AB or 3C, indicating that vaccination had prevented, or severely limited, viral replication (Berger et al., supra). Interestingly, one of the BEI-inactivated vaccine-vaccinated animals (#101) showed an increase in antibodies to structural proteins and the appearance of reactivity with 3D following challenge, suggesting that limited, but clearly detectable, viral replication had taken place in the face of challenge in this animal. The possibility that virus replication occurred in this animal is consistent with the finding that this animal showed the lowest prechallenge titer of neutralizing antibodies (Table 5).

This challenge study demonstrates that the RGD-deleted vaccine performed as well as, or exceeded, the accepted BEI-inactivated vaccine with respect to protection from challenge, generation of serum neutralizing antibodies, and generation of an immune response which restricts replication of the virus upon challenge. This is the first demonstration that a safe and effective vaccine can be prepared by genetically removing the cell binding site from a virus.

Example 5

Growth of Wild-Type FMDV in Cell Cultures

Transfected and wild-type cell cultures as shown in Table 3 were second-passage, G418-selected cells or wild-type cells. Cells were grown in 35 mm Petri dishes, infected at a multiplicity of infection (moi) of 20 for one hour at 37° C., rinsed in MES-buffered saline, pH 6.0 to remove input virus, incubated overnight at 37° C., lysed by freeze/thaw and titers determined by plaque assay. Virus yields (pfu/ml) are shown in Table 3.

All references cited hereinabove are herein incorporated by reference.

We claim:

1. A method of making a genetically-engineered cell line which is susceptible to infection by foot-and-mouth disease virus and allows said virus to replicate, said method comprising a) selecting a cell line;

b) selecting cell surface protein intracellular adhesion molecule 1 and obtaining the DNA encoding said protein;

c) selecting an antibody specific for foot-and-mouth disease virus and obtaining the DNA encoding said antibody;

d) fusing the DNA encoding the intracellular adhesion molecule 1 and the DNA encoding the antibody to form a chimeric DNA;

e) inserting the chimeric DNA into a eucaryotic expression plasmid;

f) transfecting the cell line of step a) with the plasmid of step e); and g) selecting a transformed cell line having a cell surface receptor protein expressed by the chimeric DNA wherein said cell surface receptor protein binds to foot-and-mouth disease virus, resulting in infection and in replication of foot and mouth disease virus.

2. The method of claim 1, wherein the cell line is a Chinese hamster ovary cell line.

3. The method of claim 1, wherein the antibody is a monoclonal antibody.

4. A genetically-engineered cell having susceptibility to infection by foot-and-mouth disease virus and allowing foot-and-mouth disease virus to replicate, wherein said cell expresses a chimeric cell surface receptor comprising cell surface protein intracellular adhesion molecule 1 fused to an antibody specific for foot-and-mouth disease virus.

5. The cell of claim 4, wherein said antibody is a monoclonal antibody.

* * * * *